US009220854B1

(12) United States Patent
    Okrusko

(10) Patent No.: US 9,220,854 B1
(45) Date of Patent: Dec. 29, 2015

(54) BREATH BELLOWS

(76) Inventor: Mark Okrusko, Santa Barbara, CA (US)

( * ) Notice: Subject to any disclaimer, the term of this patent is extended or adjusted under 35 U.S.C. 154(b) by 351 days.

(21) Appl. No.: 12/939,608

(22) Filed: Nov. 4, 2010

Related U.S. Application Data

(63) Continuation-in-part of application No. 11/615,990, filed on Dec. 24, 2006, now abandoned.

(51) Int. Cl.
*A61M 16/00* (2006.01)
*A61M 16/20* (2006.01)
*A61M 15/08* (2006.01)
*A61M 16/08* (2006.01)

(52) U.S. Cl.
CPC .............. *A61M 16/00* (2013.01); *A61M 16/08* (2013.01); *A61M 16/20* (2013.01)

(58) Field of Classification Search
CPC ..... A62B 7/00–7/04; A62B 9/00; A62B 9/02; A62B 9/06; A62B 33/00; A62B 15/00; A61M 16/08; A61M 16/10; A61M 16/20; A61M 16/208; A61M 16/0488; A61M 16/049; A61M 16/00; A61M 16/0075; B63C 11/00; B63C 11/02; B63C 11/18; B63C 11/184; B63C 11/186; B63C 11/205; B63C 11/22; B63C 9/08; B63C 9/087; B63C 9/105; B63C 9/11; B63C 9/125; B63C 9/13; B63C 9/15; B63C 9/155
USPC .............. 128/200.24, 202.13, 202.19, 203.22
See application file for complete search history.

(56) References Cited

U.S. PATENT DOCUMENTS

| | | | | |
|---|---|---|---|---|
| 4,365,628 A * | 12/1982 | Hodel | ....................... | 128/205.12 |
| 5,048,536 A * | 9/1991 | McEwen | ........................ | 600/561 |
| 5,660,477 A * | 8/1997 | Ichikawa | .......................... | 383/80 |
| 5,911,406 A * | 6/1999 | Winefordner et al. | ........ | 251/339 |
| 8,166,969 B2 * | 5/2012 | Hall et al. | ................. | 128/202.15 |
| 2002/0124294 A1* | 9/2002 | McKenzie et al. | .................... | 2/69 |
| 2002/0148467 A1* | 10/2002 | Bosse et al. | ............. | 128/201.27 |
| 2006/0225217 A1* | 10/2006 | Jakubowski | ................... | 5/655.3 |
| 2008/0185408 A1* | 8/2008 | James | ......................... | 224/148.2 |
| 2010/0264175 A1* | 10/2010 | Fidrych et al. | ............. | 224/148.2 |
| 2011/0043755 A1* | 2/2011 | Gibson-Horn et al. | ........ | 351/203 |

* cited by examiner

*Primary Examiner* — Rachel Young
(74) *Attorney, Agent, or Firm* — Koppel, Patrick, Heybl & Philpott

(57) ABSTRACT

The present disclosure involves a breathing apparatus that is particularly well suited for use by water sports enthusiasts. The device provides a breath of air to a swimmer or surfer at depth without the use of compressed air tanks. Physically innocuous to the wearer, the device can be repeatedly recharged with minimal interruption to the sports activity.

8 Claims, 3 Drawing Sheets

BREATH BELLOWS

This application is a Continuation-In-Part of application Ser. No. 11/615,990 filed Dec. 24, 2006.

The present invention relates to a breathing apparatus that provides air to a swimmer without the use of compressed air tanks.

BACKGROUND AND PRIOR ART

Diving, surfing and other water sports are intricately woven into the fabric of American culture. Because the human mammalian respiratory system is not designed to function under water however, breathing devices have been developed over the years to compensate for this lack of functionality. The sophistication of such devices is driven by the demands of the particular water activities with which each is associated. Deep sea diving requires bulky complex apparatus, for instance, while the demands of swimming and surfing are relatively modest by comparison.

The needs of swimmers and surfers are generally served by lightweight devices such as snorkels, small air tanks, and small air reservoirs. Sometimes, these devices are an integral part of the intended activity. At other times, however, they are not and a water sports enthusiast may find themselves caught in a situation that is beyond their experience or physical capabilities. More particularly, a swimmer or surfer may become submerged for longer periods of time than is either safe or comfortable. An extra breath of air in such a scenario can play a significant role in diverting a tragic outcome.

Snorkels and other devices involving a conduit between the person's mouth and air above the surface of the water are limited to depths determined by the dimensions of the apparatus. Furthermore, unless the swimmer is engaging in the sport of "snorkeling", they impede the action of the intended sport, interfering with its performance, its enjoyment, and its safety. Several examples of such devices can be found in the prior art including U.S. Pat. Nos. 7,047,965, 6,408,844, 5,697,362, and 4,583,536.

Face masks can also be used by swimmers and surfers. However, the air supplied within the volume of the face mask is limited. Furthermore, the mask interferes with the wearer's field of view and is easily dislodged from its intended position. The former consideration is of paramount concern to surfers, who are heavily dependent upon their visual senses in order to negotiate the wind, waves, and other surfers with agility and accuracy. An example of a face mask with an air reservoir is disclosed in publication no. 2001/0012446.

Small tanks and other such reservoirs are capable of providing air at modest depths. Tanks are obviously inappropriate for surfing. Although some systems involving small reservoirs are available, they generally require a significant effort to use and recharge. To date, an air supply system that provides an emergency breath of air, is easily recharged, and remains physically innocuous to the user, is simply unavailable.

SUMMARY

It is an object of the present invention to provide a breathing apparatus to a person engaging in water sports that can be repeatedly refilled with minimal interruption to the sports activity.

It is an object of the present invention to provide a breathing apparatus to a person engaging in water sports that is functional while being completely submerged in water.

It is an object of the present invention to provide a breathing device to a person engaging in water sports that is devoid of tanks and other bulky apparatus.

It is an object of the present invention to provide a breathing apparatus to a person engaging in water sports that does not interfere with the activity of the sport.

It is an object of the present invention to provide a breathing apparatus that is simple to manufacture, simple to use, and is affordable to the average water sports enthusiast.

The above needs are met by an apparatus that provides an extra breath of air for a person submerged in water comprising a garment, a bladder attached to the garment, and an air hose with a bite valve attached to the bladder. The garment, adapted to be worn by the person, snugly fits the upper part of the person's torso. The bladder is congruent with the garment.

The bladder comprises a front bellows surface, a back bellows surface, and a pliable interface therebetween. The front bellows surface is rigid and airtight, the back bellows surface is rigid and airtight, and the pliable interface is flexible and airtight. The front bellows surface is connected to the pliable interface via an airtight seam and the back bellows surface is connected to the pliable material via an airtight seam. The front bellows surface, the back bellows surface, and the interface material define an enclosed volume therebetween, and the enclosed volume defines an air reservoir.

A tubular conduit comprising a hose and a bite valve is in fluid communication with the air reservoir. The hose has a first end and a second end. The first end of the hose is attached to the front bellows surface, for example, a central portion of the front bellows surface, and is in fluid communication with the air reservoir. The second end of the hose is attached to the bite valve. When the hose is extended and the bite valve pinched open, air streams into the air reservoir, thus recharging an empty reservoir with air. The method of using the breath bellows to provide a breath of air to a swimmer or surfer comprises the steps of inserting the bite valve into the mouth, opening the bite valve with the teeth and drawing in a breath of air. Thus, the wearer of the breath bellows is provided with an extra breath of air for emergency situations.

Alternate embodiments may include any combination of the following:

The air reservoir can further comprise an inner lining congruent with the enclosed volume.

The bellows attachment of the front and back surfaces at the circumference can further comprise an application of liquid tape.

The garment can further comprise means for further snugging the garment to the person's torso.

The features of the invention believed to be novel are set forth with particularity in the appended claims. However the invention itself, both as to organization and method of operation, together with further objects and advantages thereof may be best understood by reference to the following description taken in conjunction with the accompanying drawings.

DESCRIPTION OF THE PREFERRED EMBODIMENTS

The term, "bite valve", as used herein, is intended to describe a common device that can be opened by the application of pressure with a person's teeth or with the fingers.

DESCRIPTION OF NUMERALS USED IN THE FIGURES

10—breath bellows
20—supporting garment
21—bladder defining an internal air reservoir
22—hose
23—bite valve
24—circumference, interface between front and back bellows surfaces
30—adjustment tabs
31—front bellows surface
32—back bellows surface
33—pliable interface material
34—optional interior lining

DETAILED DESCRIPTION OF THE PREFERRED EMBODIMENT

Figure 1:
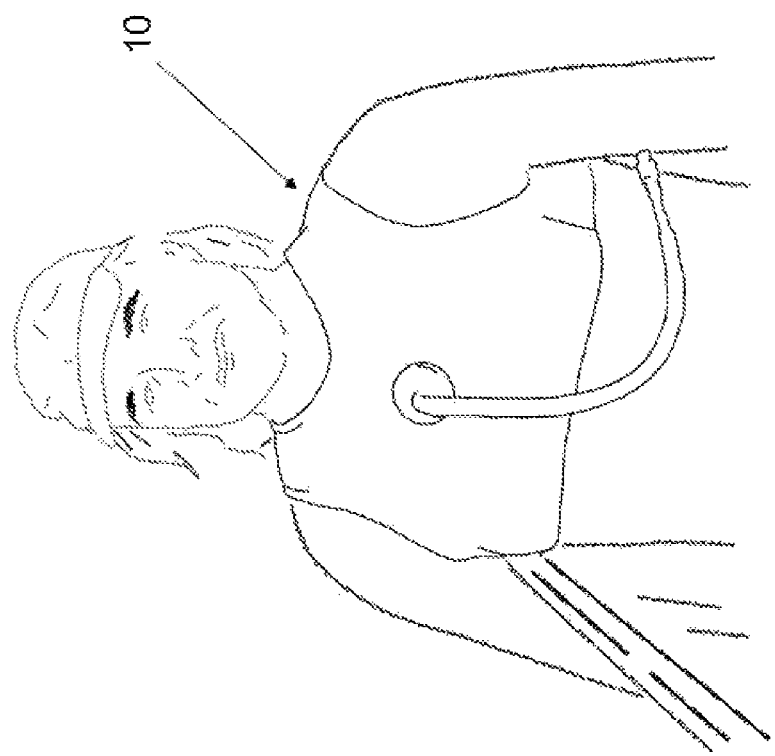
FIG. 1 shows a surfer wearing the breath bellows.
Figure 2:
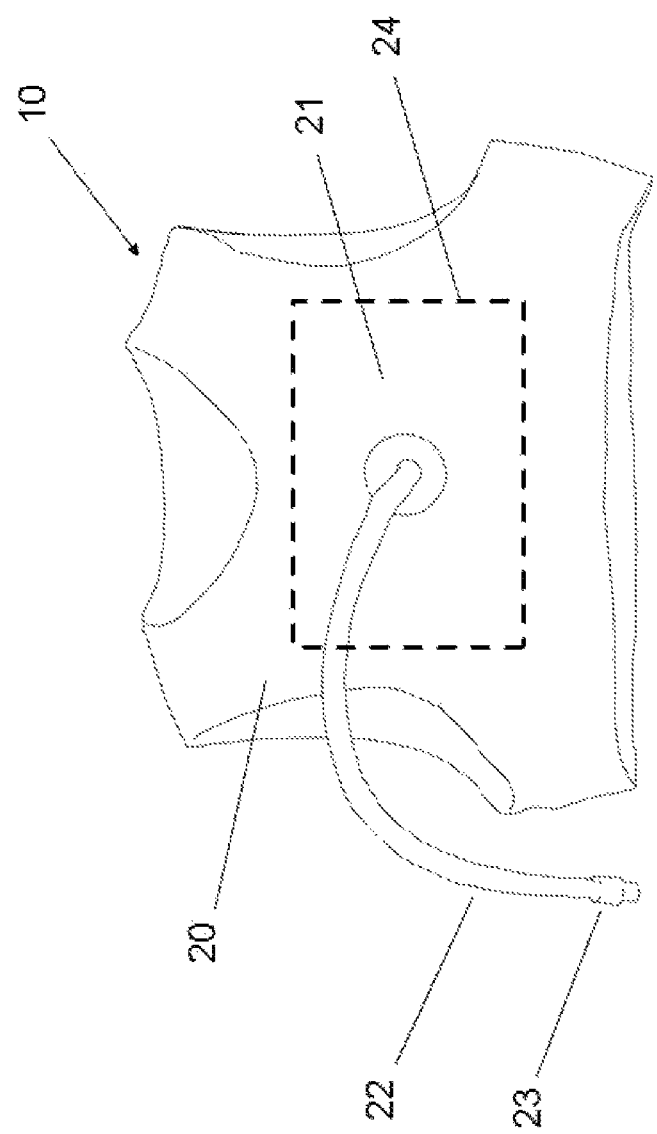
FIG. 2 illustrates the basic features of breath bellows indicating the supporting garment structure, a bladder defining an internal air reservoir, and a hose connecting the internal reservoir to a bite valve. Side adjustment tabs are shown in the following figure.

FIG. 2 illustrates the main features of the breath bellows (10). The supporting garment (20) is designed to snug the upper part of the wearer's chest as indicated in FIG. 1. The bladder defining an internal air reservoir (21) is comprised of a front bellows surface (31), and a back bellows surface (32) that are similarly dimensioned and mutually attached to a pliable interface material (33). All interface seams between the interface/front surface and interface/back surface must waterproofed via liquid tape or other means.

The front bellows surface (31) must be rigid and airtight. The back bellows surface (32) and the interface material (33) must be airtight as well. In order to provide the necessary rigidity for a bellows operation, the back bellows (32) surface may simply lie snugly against the body or it may incorporate an auxiliary rigid surface. Both the front bellows surface (31) and the back bellows surface (32) may be lined to further fortify the bellows quality of the volume defined therebetween.

The hose (22) is flexible, bellows, has a bite valve (23) at one end and connects to the internal reservoir of the bladder (21) at the opposite end. The bite valve (23) can be opened by a person's teeth, or by simply pinching with the fingers. When opened, the bite valve (23) enables fluid communication between the hose (22), the internal reservoir of the bladder (21), and the outside air. When closed, the bite valve (23), hose (22) and bladder (21) contain a volume of air that is confined until such time as it is actuated by a person's teeth or fingers.

Figure 3B:
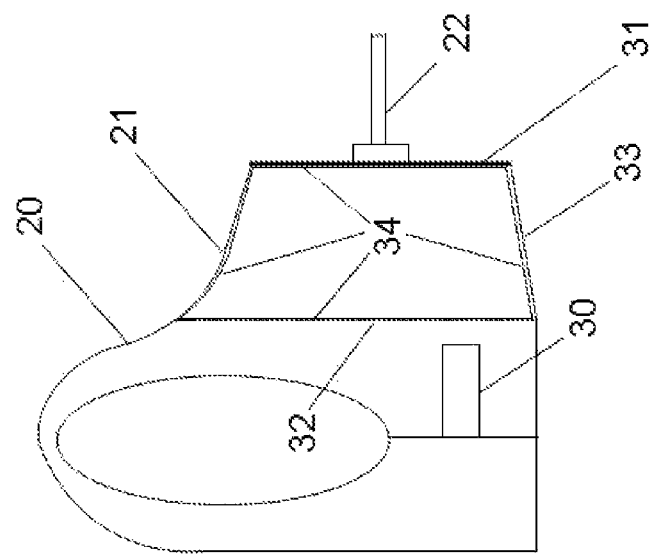
FIG. 3 shows side views of breath bellows indicating deflated (FIG. 3a) and inflated (FIG. 3b) configurations of the bladder.
Figure 3A:
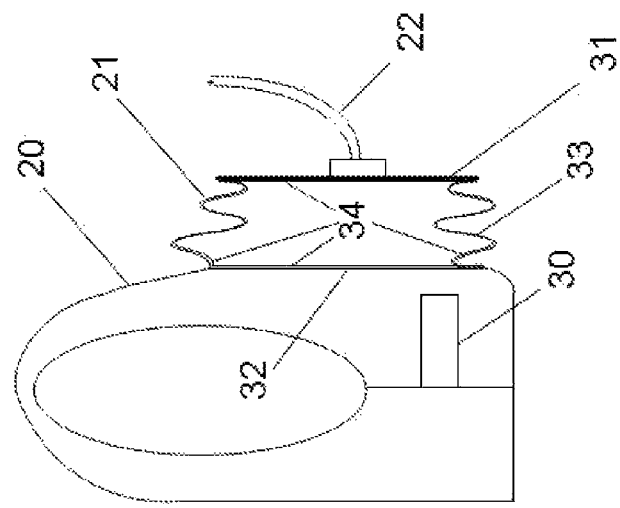

FIG. 3 illustrates the method wherein the reservoir is "recharged" with air. In its deflated state, the bladder (21) is defined by the front bellows surface (31), the back bellows surface (32), and the unextended interface material (33). In this configuration, the internal volume defined by the bladder (21) is minimal, as is the amount of air confined within its internal air reservoir. To "recharge" or fill the air reservoir with air, the user simply pulls on the hose (22) while pinching the bite valve (23) open and exposing it to the outside air, as shown in FIG. 3b. Because the hose (22) is attached only to the front bellows surface (31), for example, at a portion thereof substantially central to the length and width of the front bellows surface (31), pulling the hose (22) also pulls the front bellows surface (31) away from the back bellows surface (32), creating a larger volume of space therebetween. If the bite valve (23) is open, the vacuum defined by this newly created volume is quickly filled with air. The bite valve (23) can then be closed, trapping the newly captured air within the bladder (21). When the user requires a breath of air, the bite valve can again be opened by the person's teeth. When not being used, the hose (22) can then be secured by a small loop or tucked away under the rim of the garment (20) until such time as needed by the user.

While particular embodiments of the present invention have been illustrated and described, it would be obvious to those skilled in the art that various other changes and modifications can be made without departing from the spirit and scope of the invention. For example, an alternate embodiment includes an inner lining congruent with the enclosed volume and configured so as to be in fluid communication with the hose (22). The bellows attachment of the front and back surfaces with the interface material may comprise an application of liquid tape. The garment may comprise a rigid insert, for example, to further snug the garment to the person's torso. It is therefore intended to cover in the appended claims all such changes and modifications that are within the scope of this invention.

The invention claimed is:

1. A device configured to provide breathable air to a user submerged underwater, comprising:
   a garment adapted to fit said user's torso;
   a bladder congruent with said garment, said bladder comprising a bellowed structure which comprises a front surface, a back surface, and a pliable interface therebetween, said bellowed structure defining an air reservoir, said back surface being connected to said garment such that it is substantially stationary and said front surface is configured to be moveable in relation to said back surface; and
   a conduit in fluid communication with said air reservoir, said conduit configured to allow a user to access breathable air stored in said air reservoir via a valve, wherein said conduit is connected to a substantially central location along both the length and width of said front surface such that pulling on said conduit moves said front surface away from said substantially stationary back surface.

2. The device of claim 1, wherein said valve is configured to open in response to the application of pressure.

3. The device of claim 1, wherein said air reservoir is configured to fill with breathable air in response to opening said valve and extending said conduit while said device is not submerged and is in an environment with breathable air.

4. The device of claim 1, wherein said air reservoir further comprises an inner lining.

5. The device of claim 4, wherein said inner lining is configured to fortify the volume of air in said air reservoir.

6. The device of claim 1, wherein said garment is configured to fit snugly about said user's torso.

7. The device of claim 1, wherein said back surface is configured to lie snugly against said user's body.

8. The device of claim 1, wherein said bellowed structure is waterproofed via liquid tape.

* * * * *